United States Patent [19]

Lee et al.

[11] Patent Number: 4,966,970
[45] Date of Patent: Oct. 30, 1990

[54] PROCESS FOR MANUFACTURING PYRAZINES

[75] Inventors: Young K. Lee; Sang-Eon Park; Young S. Kwon, all of Daejon-si, Rep. of Korea

[73] Assignee: Korea Research Institute of Chemical Technology, Rep. of Korea

[21] Appl. No.: 291,455

[22] Filed: Dec. 29, 1988

[30] Foreign Application Priority Data

Dec. 31, 1987 [KR] Rep. of Korea ............ 15641

[51] Int. Cl.$^5$ .......................... C07D 241/12
[52] U.S. Cl. ................................ 544/410
[58] Field of Search ........................ 544/410

[56] References Cited

U.S. PATENT DOCUMENTS

| | | | |
|---|---|---|---|
| 2,400,398 | 5/1946 | Dixon | 544/410 |
| 2,414,552 | 1/1947 | Pfann et al. | 544/410 |
| 2,945,858 | 7/1960 | Tarailo | 544/410 |
| 3,005,820 | 10/1961 | Cenker et al. | 544/410 |
| 3,067,199 | 12/1962 | Langdon | 544/410 |
| 4,097,478 | 6/1978 | Sata | 544/410 |
| 4,762,929 | 8/1988 | Rebafka | 544/410 |

FOREIGN PATENT DOCUMENTS

| | | |
|---|---|---|
| 466652 | 7/1950 | Canada ............ 544/410 |
| 2722307 | 3/1978 | Fed. Rep. of Germany . |
| 49-30383 | 3/1974 | Japan . |
| 49-25947 | 7/1974 | Japan . |
| 54-27577 | 9/1979 | Japan . |
| 55-45610 | 3/1980 | Japan . |
| 55-122769 | 9/1980 | Japan . |
| 258168 | 12/1985 | Japan ............ 544/410 |
| 2294667 | 12/1987 | Japan ............ 544/410 |
| 82719 | 4/1982 | Rep. of Korea . |
| 00189 | 1/1988 | World Int. Prop. O. ......... 544/410 |

OTHER PUBLICATIONS

Kitchen et al., J. Org. Chem. 8, 342 (1943).
Okada et al., Chem. Abst. 74-141692s (1971).
Okada et al., Chem. Abst. 88-190746k (1978).
Fujita et al., Chem. Abst. 93-239457m (1980).
Connor et al., J.A.C.S., vol. 54, pp. 1138-1145.
Kajiyama et al., CA105568s (1974).
Sato, Chem. Abst. 88-170196c (1978).
Sanwaka Junyaku Co., Ltd. Chem. Abst. 94-103430k.
A. Andersons et al., CA-61625s (vol. 66, 1967).
Appl. Catal., 29 (1987) 161-174.

Primary Examiner—Cecilia Shen
Attorney, Agent, or Firm—Browning, Bushman, Anderson & Brookhart

[57] ABSTRACT

Pyrazines having the formula (I)

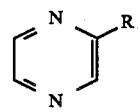

(I)

wherein R is H, methyl, or ethyl are prepared by passing a hydrogen stream containing corresponding diamines having the formula (II)

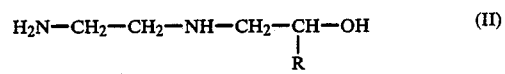

(II)

wherein R is same as previously defined, over a copper-chromite catalyst which has been once reduced at 300°-450° C. in a hydrogen-containing stream.

3 Claims, No Drawings

PROCESS FOR MANUFACTURING PYRAZINES

BACKGROUND OF THE INVENTION

1. Field of the Invention

This invention relates to a process for the manufacture of pyrazine by catalytic dehydrocyclization of diamines. This process has experienced a problem of low selectivity which has remained unresolved in many cases.

2. Description of the Background

Copper-chromite catalysts have been used for this reaction. Additionally, other methods for the preparation of pyrazine are also known.

Korean Pat. No. 82-719 describes that 3.2 grams of alkylpyrazine was obtained after 1.5 hours of reaction time from 5 grams of N-(2-alkylhydroxy)ethylenediamine by the direct dropping of the reactant which was vaporized in to top of reactor, followed by extraction with ether, drying with anhydrous magnesium sulfate, and evaporating the ethylether. The catalyst was activated at 350° C. with 4 liters of air for 2 hours followed by 1 liter of hydrogen for 1 hour. The process has the disadvantage of low production capacity, because of 0.17 hour$^{-1}$ of weight hourly space velocity, which is the feed rate of reactant in weight per hour to the unit weight of catalyst. Also, a low yield of 80% was obtained. As disclosed in Japan Pat. (kokai) No. 55-122,769, the catalyst was activated by treating with a hydrogen stream diluted with nitrogen for 18 hours at a relatively low temperature of 170°-200° C. The catalyst was pelletized CuO—Cr$_2$O$_3$ of 1 to 1.25 weight ratio (CuO to Cr$_2$O$_3$) with 5% of pulverized carbon and water. It has the advantages of a lower treating temperature for the catalyst and a reaction temperature of 265°-300° C., but the disadvantages of a long treatment time with hydrogen, a low conversion of 82%, and a low yield of 78%.

Conventional methods for the preparation of pyrazines from different reactants are disclosed in the following patents: German Pat. No. 2,722,307; Japanese Pat. No. 49-25,947; Japan Pat. (kokai) No. 49-30,383; Japan Pat. (kokai) No. 54-27,577; and Appl. Catal., 29.161 (1987). The conventional methods of preparing pyrazines described hereinabove have disadvantages of obtaining low yield. This implies that piperazines and multi-alkylated (more than 2) pyrazines may be formed together, and also pose difficulties in separation because of difficult control of the distillation process due to a high portion of by-products.

SUMMARY OF THE INVENTION

To improve the disadvantages described hereinabove, this invention relates to the preparation of pyrazines having the formula:

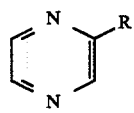
(I)

wherein R is H, methyl, or ethyl from diamines having the formula:

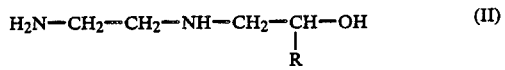

wherein R is same as previously defined, with more than 90% yield and 97% conversion by the vapor phase catalytic reaction through improving the catalyst treatment and changing the carrier gases. The catalyst used is a copperchromite (copper: 20-80%; chromium: 20-80%, barium or manganese: 5-20%), which is reduced by a hydrogen stream diluted in nitrogen at a temperature range of from room temperature to 300°-450° C. Hydrogen diluted in nitrogen or hydrogen without nitrogen is used as a carrier gas. The starting material (II) can be easily prepared from condensation of diamine with alkylene oxide by referring to the method of Kichin and Polad [J. Org. Chem., 8,342 (1943)].

This invention has the characteristics of preventing the deactivation of the catalysts and increasing the selectivity of pyrazines (I) by vapor phase catalytic reaction. In addition, it has the characteristics of simplifying the separation and purification process due to produce very small quantities of by-products.

DESCRIPTION OF THE PREFERRED EMBODIMENTS

Copper-chromite catalyst of this invention was prepared from the precipitation method of Atkins [J. Amer. Chem. Soc., 54,1138 (1932)], and then coprecipitated in ammonia water after adding Ba or Mn compounds. It was pelletized after adding alumina or carbon. Alumina or carbon can be added as a coagulation agent, and Ba or Mn has the effect of protecting the catalyst from deactivation. The prepared copper-chromite catalyst has the CuO and CuCr$_2$O$_4$ phases obtained by calcination, and then reduced under a hydrogen stream diluted in nitrogen. The reduced copper-chromite catalyst of this invention has a great effect on the conversion of the reactants and the selectivity on the pyrazines produced. In addition, the reduction state of the reduced copper-chromite catalyst in dehydrocyclization for pyrazines is important. The reactivity of the catalyst was obtained in maximum efficiency by reducing with a hydrogen stream of gradually increased concentration in the nitrogen from low to neat, i.e., all hydrogen, and increasing the reduction temperature from room temperature to high temperature, instead of reducing directly with hydrogen at high temperature. The reduction temperature must be over 300° C., but not exceed 450° C. The major phase of copperchromite catalyst reduced at 300°-450° C. was Cu(O) by X-ray diffraction analysis, so that the Cu(O) phase could be active for the reaction of diamines. However, the maximum activity of catalyst is obtained by preventing the Cu(O) phase from sintering to copper metal at the high temperature because the reduction of copper-chromite with hydrogen is an exothermic reaction (CuO+H$_2$→Cu+H$_2$O, $\Delta H = -20.7$ kcal/mole at 250° C.). The catalyst reduced at lower than 300° C. has not only low activity, but low selectivity on pyrazines. It is considered an incomplete reduction at such low temperatures. On the other hand, activity and selectivity were decreased at a reduction temperature above 450° C., because of the active sites of the catalyst decreasing by the severe sintering to copper metal. In the preparation of pyrazines from N-(2-alkylhydroxy)ethylenediamines by dehydration and dehydrocyclization, the copper-chromite catalyst with the most effective active sites is obtained by reduction at a temperature of from room temperature up to 450° C., preferably from about 300°–450° C. In addition, the high selectivities on pyrazines are obtained at 3 or less of weight hourly space velocity. The selectivities and the conversions are decreased rapidly at above 3 of weight hourly space velocity. The selectivities are more apt to be influenced than conversions according to the reaction temperature over reduced copper-chromite catalysts. The optimum reaction temperatures are 300°–450° C. Piperazines which are incompletely dehydrogenated products are produced at the low reaction temperature. Cracked compounds are produced at the high reaction temperatures. These by-products cause the activity of catalyst to decrease. The activity of the deactivated catalyst can be completely recovered with regeneration by re-reducing the catalyst with hydrogen after air treatment.

The process results in over a 97% conversion of the diamines with over 90% (by mole) yield of alkylpyrazine. Also, the catalysts exhibit long lifetimes and high activity.

The following examples are provided to illustrate the invention. In these examples, all parts and percentages are by mole unless otherwise specified.

EXAMPLE 1

The 20 grams of copper-chromite catalysts were prepared by the precipitation methods from copper nitrate and chromium solutions, which could be the ratio of CuO to $Cr_2O_3$ as 4:1 by weight, with manganese chloride, that could be 10% by weight, followed by calcination at 350° C. These calcined catalysts were loaded in a tubular reactor made of 1" pyrex glass, and then treated with hydrogen in nitrogen gas varying from 2 to 50% at a flow rate of 200 ml/min., up to 350° C. with 2° C./min. of temperature programming rate.

Over this reduced catalyst, 20 grams/hr of N-(2-ethylhydroxy)ethylenediamine was fed with 50% of hydrogen in nitrogen at 350° C. using a micro metering pump. The product, pyrazine (14.2 grams), was obtained for 1 hour of reaction time Product streams were analyzed using a Gas Chromatograph equipped with OV-17 (10% by weight) column. Conversion was ca. 100% with 92.8% of selectivity.

EXAMPLE 2

With the same catalyst and reaction conditions as those of Example 1, 15.5 grams of methylpyrazine was obtained by the feeding of 20 grams of N-(2-propylhydroxy)ethylenediamine for 1 hour. Gas chromatographic analysis gave around 100% conversion and 97.3% selectivity on methylpyrazine.

EXAMPLE 3

With the same catalyst and reaction conditions as those of Example 1, 15.8 grams of ethylpyrazine were obtained by the feeding of 20 grams of N-(2-butylhydroxy)ethylenediamine for 1 hour. Gas chromatographic analysis gave ca. 100% conversion and 96.4% selectivity on ethylpyrazine.

EXAMPLE 4

BaO was introduced instead of MnO in the catalyst of Example 1. Over this catalyst, 20 grams of N-(2-propylhydroxy)ethylenediamine converted into 14.6 grams of methylpyrazine under the same reaction conditions as those of Example 1. Conversion was complete and the selectivity on methylpyrazine was 91.6%.

EXAMPLE 5

A catalyst was prepared as in the method of Example 1 except not combining MnO. The 15.2 grams of methylpyrazine was obtained from the 20 grams of N-(2-propylhydroxy)ethylenediamine under the same reaction conditions of those in Example 1. Selectivity on methylpyrazine was 95.4% with complete conversion.

COMPARISON 1

This comparison demonstrates the need for using hydrogen flow during the reaction in order to achieve not only high conversion of diamines and high selectivities on corresponding pyrazines but also long lifetime of the catalysts.

0.5 grams of catalysts used in Example 5 was reduced by the method of Example 1. To investigate the difference between the cases of hydrogen flowing and nitrogen flowing, N-(2-propylhydroxy)ethylenediamines with 1 hour$^{-1}$ of space velocity were reacted at 390° C. of reaction temperature.

In the case of hydrogen flowing during the reaction, conversions were over 97% and selectivities on methylpyrazine were over 95% (mol) throughout the reaction times tested. On the other hand, in the case of nitrogen flowing during the reaction instead of hydrogen, conversions were drastically reduced with much lower selectivities. The results are shown in Table I below.

TABLE I

| Effects of Flowing Gas on Conversion and Selectivity | | | | | | | |
|---|---|---|---|---|---|---|---|
| Flowing Gas | Hydrogen | | | | Nitrogen | | |
| Reaction Time (hr) | 1 | 2 | 3 | 4 | 1 | 2 | 3 | 4 |
| Conversion | 98.9 | 97.9 | 97.6 | 97.0 | 88.2 | 71.0 | 59.9 | 52.2 |
| Selectivity | 96.5 | 97.9 | 96.1 | 95.0 | 66.0 | 52.7 | 38.4 | 28.7 |

Hence, the characteristics of this invention are that the rather higher reduction temperature for activating copper-chromite catalysts and the hydrogen flowing during the reaction of diamines could give high activities and selectivities on pyrazines with the longer lifetime of catalysts. So then, this process could have a merit that would be economic due to the lower production of byproducts, long time intervals for catalyst change, and simple separation process.

What is claimed is:

1. A process for manufacturing pyrazines having the formula

from N-(2-alkylhydroxy)ethylenediamines having the formula

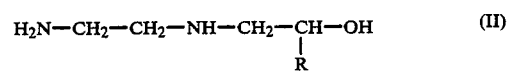

where R is H, methyl or ethyl, by passing said diamines in a hydrogen-containing stream, at reaction temperatures of from about 300° to about 450° C., over a copper-chromite catalyst reduced with a hydrogen-containing stream at temperatures of from 300° to 450° C.

2. The process of claim 1 wherein said hydrogen-containing stream contains an inert gas.

3. The process of claim 2 wherein said inert gas is nitrogen.

* * * * *